United States Patent [19]

Stiefel

[11] Patent Number: 4,957,747

[45] Date of Patent: Sep. 18, 1990

[54] METHOD OF TREATING AGED SKIN

[75] Inventor: Werner K. Stiefel, Coral Gables, Fla.

[73] Assignee: Stiefel Laboratories, Inc., Coral Gables, Fla.

[21] Appl. No.: 351,825

[22] Filed: May 15, 1989

[51] Int. Cl.$^5$ ............................................. A61K 33/08
[52] U.S. Cl. ..................................................... 424/691
[58] Field of Search ......................................... 424/691

[56] References Cited

FOREIGN PATENT DOCUMENTS 1021276 3/1966 United Kingdom .

*Primary Examiner*—Leonard Schenkman
*Attorney, Agent, or Firm*—Mathews, Woodbridge & Collins

[57] ABSTRACT

The firmness and tone of aged skin is improved by repeatedly applying a fluid topical composition containing a suspension of fine particles of a non-absorbable aluminum oxide abrasive in a topically acceptable aqueous base of sodium cocoisethionate, at least one emollient, and a suspending agent.

8 Claims, No Drawings

METHOD OF TREATING AGED SKIN

The present invention relates to a method of improving the firmness and tone of aged skin.

BACKGROUND OF THE INVENTION

PCT Application 8606275 describes a cosmetic preparation containing resinol, a volatile silicon, and a mutual solvent which reduces facial lines and wrinkles, increases skin elasticity, reduces pore size, and improves skin texture.

U.S. Pat. No. 4,603,146 to Kligman describes a method of retarding and reversing the loss of collagen fibers, abnormal changes in elastic fibers, and the deterioration of small blood vessels by the application of vitamin A acid (all-trans retinoic acid).

U.S. Pat. No. 3,092,111 to Saperstein et al. describes a method for the therapeutic abrasion of human skin in the treatment of acne by repeatedly rubbing the skin with a paste of an inorganic abrasive until dryness, redness, and desquamation occur.

DETAILED DESCRIPTION

The present invention pertains to a method of improving the firmness and tone of aged skin which comprises repeatedly applying a fluid topical composition containing a suspension of fine particles of a nonabsorbable aluminum oxide abrasive in a topically acceptable aqueous base comprising sodium cocoisethionate, at least one emollient, and a suspending agent. By the term aged skin is meant both intrinsically aged skin (resulting from the normal aging process) and photoaged skin (resulting from over-exposure to ultraviolet light).

The topical composition is fluid in nature, typically a paste, which can be readily dispensed and rubbed on the skin. This composition will contain from about 35% to about 65%, by total weight of the composition, of fine aluminum oxide particles. Typically the majority of the aluminum oxide particles, that is 80% or more, will have a particle size ranging from $170\mu$ to $600\mu$ with 40 to 50% falling in the $250\mu$ to $420\mu$ range.

The aqueous base of the composition will comprise from about 5% to about 10%, by total weight of the composition, of sodium cocoisethionate and from about 5% to about 10% of at least one emollient. The emollient will include at least one of member, and preferably several members, selected from the group consisting of polyethylene glycol, fatty acid esters of polyols, dimethicone, and alkyl esters of fatty acids. Typical emollients thus include polyethylene glycol 75, glyceryl stearate, polyethylene glycol 75 stearate, dimethicone, octyl hydroxystearate, and the like.

The aqueous base of the composition also will contain an effective amount of a suspending agent to facilitate maintenance of the aluminum oxide suspension. While a variety of known suspending agents can be employed, bentonite is particularly preferred since it also has the property of adsorbing excess oil from the surface of the skin.

The liquid topical composition also will contain from about 20% to about 50% by weight of water.

In addition, other excipients can be present, as for example humectants such as glycerine, foam boosters such as diethyl lauramide, soaps such as the sodium salts of fatty acid such as stearic acid, myristic acid, lauric acid, and the like, preservatives and antioxidants such as chloroxylenol, Dowicil 200, BHT, and the like, fragrances, and dyes. Typically these additional components are present in minor amounts, i.e., less than about 2% and often less than 1%.

The composition is applied topically several times daily with a slight rubbing action. In contrast to prior art agents such as all-trans retinoic acid, the composition is not intended to produce severe irritation, dryness, or redness. Rather, the treated skin becomes tighter, smoother, and slightly shiny in the course of treatment. Some minor dermatitis may appear during this therapy but can be treated readily with a topical antiinflammatory agent such as hydrocortisone cream. The following are typical formulations:

EXAMPLE 1

| Ingredient | Amount (weight) |
| --- | --- |
| Aluminum oxide (Bento Grit Fine) | 38.020 |
| Sodium cocoisethionate | 7.1165 |
| Emollients: | |
| PEG 75 | 4.2360 |
| Glyceryl stearate/PEG 100 stearate | 1.6944 |
| Dimethicone | 1.1296 |
| Octyl hydroxystearate | 0.5648 |
| Bentonite | 4.8400 |
| Soap formers: | |
| Stearic acid | 2.5416 |
| Myristic acid | 1.1296 |
| Lauric acid | 1.1296 |
| Sodium hydroxide | 1.9203 |
| Humectant (glycerine) | 1.6944 |
| Foam builder (diethyl lauramide) | 1.6944 |
| Antioxidant/preservative | |
| Chloroxylenol | 0.1130 |
| BHT | 0.0085 |
| Water | 32.0158 |

The foregoing ingredients are thoroughly blended, optionally together with a small amount of fragrance and a pharmaceutically acceptable dye such as F.D. & C #8 or F.D. & C. #3, to form a paste-like suspension (hereinafter "fine" composition).

EXAMPLE 2

| Ingredient | Amount (weight) |
| --- | --- |
| Aluminum oxide (Bento Grit Fine) | 52.1057 |
| Sodium cocoisethionate | 5.5124 |
| Emollients: | |
| PEG 75 | 3.2812 |
| Glyceryl stearate/PEG 100 stearate | 1.3125 |
| Dimethicone | 0.8750 |
| Octyl hydroxystearate | 0.4375 |
| Bentonite | 3.0043 |
| Soap formers: | |
| Stearic acid | 1.9687 |
| Myristic acid | 0.8750 |
| Lauric acid | 0.8750 |
| Sodium hydroxide | 1.4875 |
| Humectant (glycerine) | 1.3125 |
| Foam builder (diethyl lauramide) | 1.3125 |
| Antioxidant/preservative | |
| Chloroxylenol | 0.0875 |
| BHT | 0.0066 |
| Water | 24.4052 |

The foregoing ingredients are thoroughly blended, optionally together with a small amount of fragrance and a pharmaceutically acceptable dye such as F.D. &

C #8 or F.D. & C. #3, to form a paste-like suspension (hereinafter "medium" composition).

EXAMPLE 3

The compositions of the present invention were first analysed for their stimulatory effect on desquamation and epidermopoiesis. A total of four areas were delineated on the thighs of each of eight normal healthy volunteers (two females, four males) and 5% dansyl chloride (fluorescent dye) was applied to each. Test formulations were applied to three of each of these areas (the fourth being untreated) in a randomised fashion. Each composition was rubbed into the skin for 30 seconds twice daily for three days. After the final application, assessment of fluorescence was made with a fluorescent comparator. A single 4 mm punch biopsy then was taken from each area and each sample was divided in two and subjected to autoradiographic (tritiated thymidine) and histological (epidermal cell and stratum corneum population size) analysis. There were no significant adverse effects (2 subjects indicated their skin felt sore at day 2) although one subject experienced a reaction to dansyl chloride but not to the test compositions.

The test compositions included a "fine" preparation corresponding to Example 1 and a "medium" preparation corresponding to Example 2, together with a white soft paraffin control. The results are as follows:

TABLE I

| | Dansyl Fluorescence | | | |
|---|---|---|---|---|
| Subj. | Untreated | Paraffin | Fine | Medium |
| 1 | 55 | 46 | 28 | 14 |
| 2 | 50 | 52 | 23 | 3 |
| 3 | 50 | 38 | 8 | 14 |
| 4 | 50 | 48 | 21 | 17 |
| 5 | 54 | 50 | 34 | 22 |
| 6 | 41 | 43 | 17 | 11 |
| 7 | 70 | 68 | 38 | 18 |
| 8 | 58 | 60 | 34 | 5 |
| Mean | 53.5 ± 8.3 | 50.6 ± 9.5 | 25.4 ± 10.0 | 13.0 ± 6.5 |

Histological Analysis

TABLE IIA

| | Histological Analysis | | | |
|---|---|---|---|---|
| | Mean Epidermal Thickness | | | |
| Subj. | Untreated | Paraffin | Fine | Medium |
| 1 | 63.1 | 59.2 | 72.3 | 64.4 |
| 2 | 58.0 | 62.5 | 70.5 | 75.6 |
| 3 | 72.8 | 81.5 | 90.0 | 72.1 |
| 4 | 68.0 | 78.3 | 63.2 | 81.0 |
| 5 | 62.4 | 62.0 | 92.4 | 80.4 |
| 6 | 56.2 | 62.9 | 95.4 | 84.3 |
| 7 | 79.5 | 69.5 | 72.7 | 69.7 |
| 8 | 76.0 | 60.8 | 87.8 | 80.1 |
| Mean | 67.0 ± 8.5 | 67.1 ± 8.5 | 80.5 ± 12.1 | 75.95 ± 6.8 |

TABLE IIB

| | Mean Keratinocyte Height | | | |
|---|---|---|---|---|
| Subj. | Untreated | Paraffin | Fine | Medium |
| 1 | 11.9 | 12.1 | 11.6 | 11.7 |
| 2 | 12.8 | 12.5 | 13.4 | 13.2 |
| 3 | 12.2 | 12.4 | 11.1 | 12.6 |
| 4 | 11.6 | 13.0 | 10.6 | 11.4 |
| 5 | 11.7 | 11.4 | 11.9 | 11.8 |
| 6 | 11.35 | 11.01 | 14.48 | 13.22 |
| 7 | 11.96 | 11.08 | 11.19 | 10.4 |
| 8 | 12.2 | 10.4 | 12.2 | 12.0 |

TABLE IIB-continued

| | Mean Keratinocyte Height | | | |
|---|---|---|---|---|
| Subj. | Untreated | Paraffin | Fine | Medium |
| Mean | 11.96 ± 0.5 | 11.7 ± 0.9 | 12.06 ± 1.3 | 12.04 ± 0.95 |

TABLE IIC

| | Basal Layer Length:Granular Layer Length | | | |
|---|---|---|---|---|
| Subj. | Untreated | Paraffin | Fine | Medium |
| 1 | 1.21 | 1.06 | 1.44 | 1.11 |
| 2 | 1.03 | 1.01 | 1.01 | 1.10 |
| 3 | 1.24 | 1.33 | 1.30 | 1.11 |
| 4 | 1.03 | 1.01 | 1.05 | 1.02 |
| 5 | 1.16 | 1.02 | 1.18 | 1.03 |
| 6 | 1.01 | 1.11 | 1.21 | 1.03 |
| 7 | 1.35 | 1.24 | 1.40 | 1.49 |
| 8 | 1.02 | 1.11 | 1.27 | 1.06 |
| Mean | 1.13 ± 0.13 | 1.11 ± 0.1 | 1.23 ± 0.15 | 1.12 ± 0.15 |

TABLE IID

| | Labelling Index | | | |
|---|---|---|---|---|
| Subj. | Untreated | Paraffin | Fine | Medium |
| 1 | 7.7 | 4.5 | 5.3 | 9.7 |
| 2 | 5.0 | 12.7 | 15.6 | 10.0 |
| 3 | 4.3 | 5.0 | 13.2 | 14.6 |
| 4 | 6.0 | 5.4 | 9.5 | 14.6 |
| 5 | 5.8 | 16.6 | 15.7 | 22.5 |
| 6 | 14.5 | 7.4 | 40.4 | 33.2 |
| 7 | 9.9 | 14.3 | 6.4 | 10.4 |
| 8 | 20.5 | 23.2 | 8.5 | 29.5 |
| Mean | 9.21 ± 5.6 | 11.14 ± 6.7 | 14.33 ± 11.3 | 18.06 ± 9.2 |

EXAMPLE 4

The composition of Example 1 was employed in a randomized study of twelve male and female human subjects of ages 45 to 80 having photoaged skin on the extensor aspect of the forearm. The subjects had no significant concurrent disease, no history of skin disease, and were not using any topical or system medication which might interfere with the study. All subjects had one or more of wrinkles on the face, arms, or hands, pigmented macules, and yellow discoloration.

Application was made twice daily to an 8×5 cm area which was rubbed in over a 30 second interval over a period of eight weeks. Assessments were made histometrically and autoradiographically at the end of the study on punch biopsies of treated and untreated skin. The results are as follows:

TABLE III

| | Epidermal Thickness | |
|---|---|---|
| | Micrometers | |
| Patient | Example 1 | control |
| 1 | 97.18 | 78.70 |
| 2 | 64.88 | 72.19 |
| 3 | 57.42 | 53.13 |
| 4 | 76.86 | 59.85 |
| 5 | 68.38 | 66.12 |
| 6 | 70.32 | 59.05 |
| 7 | 75.59 | 53.17 |
| 8 | 70.20 | 54.55 |
| 9 | 74.33 | 55.75 |
| 10 | 70.37 | 58.67 |
| 11 | 67.24 | 78.48 |
| 12 | 68.60 | 72.24 |
| Mean | 71.78 | 63.49 |
| s.d. | 9.10 | 9.24 |

TABLE IV

| | Autoradiographic Labelling Index | |
|---|---|---|
| | Percent | |
| Patient | Example 1 | control |
| 1 | 18.3 | 8.5 |
| 2 | 8.3 | 9.4 |
| 3 | 6.6 | 4.8 |
| 4 | 15.6 | 5.4 |
| 5 | 7.4 | 9.4 |
| 6 | 12.1 | 9.7 |
| 7 | 8.9 | 9.6 |
| 8 | 9.1 | 5.1 |
| 9 | 14.5 | 4.3 |
| 10 | 8.0 | 3.9 |
| 11 | 9.4 | 6.6 |
| 12 | 15.2 | 5.3 |
| Mean | 11.1 | 6.8 |
| s.d. | 3.7 | 2.2 |

Assessments also were made noninvasively by ultrasound A-scan, extensometry, and laser doppler flowmetry every two weeks during the course of the study in comparison to a 0.05% cream of all-trans retinoic acid (Retin A cream). These results are as follows:

TABLE V

| | Skin Thickness - Ultrasound | | |
|---|---|---|---|
| | Mean microseconds | | |
| Week | Example 1 | 0.05% Retin A | Difference |
| 0 | 1.39 ± 0.14 | 1.41 ± 0.14 | −0.02 ± 0.08 |
| 2 | 1.42 ± 0.15 | 1.44 ± 0.16 | −0.02 ± 0.10 |
| 4 | 1.47 ± 0.15 | 1.49 ± 0.16 | −0.02 ± 0.11 |
| 6 | 1.52 ± 0.20 | 1.55 ± 0.23 | −0.03 ± 0.14 |
| 8 | 1.59 ± 0.21 | 1.55 ± 0.19 | 0.04 ± 0.13 |

TABLE VI

| | Extensometry | | |
|---|---|---|---|
| | Mean g Force | | |
| Week | Example 1 | 0.05% Retin A | Difference |
| 0 | 393.33 ± 144.53 | 341.67 ± 156.84 | 51.67 ± 117.31 |
| 2 | 643.33 ± 329.98 | 463.33 ± 220.28 | 180.00 ± 283.42 |
| 4 | 833.33 ± 378.54 | 415.83 ± 174.38 | 417.50 ± 252.01 |
| 6 | 757.50 ± 304.96 | 447.50 ± 261.86 | 310.00 ± 257.19 |
| 8 | 976.67 ± 302.06 | 520.83 ± 265.47 | 455.83 ± 270.34 |

TABLE VII

| | Laser Doppler Flowmetry | | |
|---|---|---|---|
| | Mean Volts | | |
| Week | Example 1 | 0.05% Retin A | Difference |
| 0 | 0.15 ± 0.15 | 0.18 ± 0.19 | −0.02 ± 0.06 |
| 2 | 0.23 ± 0.11 | 0.19 ± 0.17 | 0.04 ± 0.19 |
| 4 | 0.28 ± 0.19 | 0.22 ± 0.18 | 0.06 ± 0.18 |
| 6 | 0.40 ± 0.47 | 0.36 ± 0.34 | 0.05 ± 0.45 |
| 8 | 0.22 ± 0.19 | 0.35 ± 0.57 | −0.13 ± 0.46 |

Clinical assessment in terms of observed differences and patient preference at the end of the study were as follows:

TABLE VIII

| Patient | Example 1 | Retin A | Comments |
|---|---|---|---|
| 1 | very shiny, tighter, and smoother | no opinion | indifferent |
| 2 | tighter, smoother, and slightly shiny | no opinion | would use Example 1 comp. |
| 3 | tighter, smoother, and slightly shiny | smoother | would use Example 1 comp. |
| 4 | shiny, tighter, and smoother | slightly smoother | pleased with skin and Example 1 comp. |
| 5 | slightly shiny, tighter, and smoother | no opinion | would use Example 1 comp. |
| 6 | tighter, slightly shiny | no opinion | indifferent |
| 7 | tight, smoother, and shiny | no opinion | good results with Ex. 1 comp. |
| 8 | tighter, smoother, and slightly shiny | no opinion | definitely would use Example 1 comp. |
| 9 | tighter, smoother, and slightly shiny | no opinion | Ex. 1 comp. good but would not continue |
| 10 | tight, smooth, and shiny | no opinion | would use Ex. 1 comp. |
| 11 | slightly shiny, tighter, and smoother | smoother | indifferent |
| 12 | slightly shiny, tighter, and smoother | smoother | would use Example 1 comp. |

In all patients, the skin treated with the composition of Example 1 had smoother, tighter, and slightly shiny skin in the area of treatment. Visually, the skin treated with Retin A was not noticeably different from the untreated surrounding skin, although 4 patients thought it felt smoother (but less so than that treated with the composition of Example 1).

Two patients presented contact dermatitis after 4 weeks of treatment, the symptoms of which disappeared after to 2 weeks upon treatment with 1% hydrocortisone twice daily. Two patients treated with Retin A complained of irritation, erythema, and edema after 2 to 4 weeks, necessitating the suspension of treatment for 4 to 5 days, after which the condition generally subsided.

What is claimed is:

1. A method of improving the firmness and tone of aged skin which comprises repeatedly applying to the aged skin a fluid topical composition containing from about 35%–65% by weight of said composition a suspension of fine particles of a non-absorbable aluminum oxide abrasive in a topically acceptable aqueous base comprising sodium cocoisethionate, at least one emollient, and a suspending agent.

2. The method of claim 1 wherein the topical composition is a cream or paste.

3. The method of claim 2 wherein 80% or more of the aluminum oxide particles have a particle size ranging from 170μ to 600μ with 40 to 50% falling in the 250μ to 420μ range.

4. The method of claim 2 wherein the aqueous base of said topical composition comprises from about 5% to about 10% by weight of said composition of sodium cocoisethionate and from about 5% to about 10% by weight of said composition of at least one emollient.

5. The method of claim 4 wherein the emollient of said topical composition comprises at least one of member selected from the group consisting of polyethylene glycol, fatty acid esters of polyethylene glycol, dimethicone, and alkyl esters of fatty acids.

6. The method of claim 1 wherein the suspending agent is bentonite.

7. The method of claim 1 wherein the topical composition is a paste containing from about 35% to about 65% by weight of said composition of aluminum oxide particles 80% or more of which have a particle size ranging from 170μ to 600μ with 40 to 50% falling in the 250μ to 420μ range; said aqueous base comprises from about 20% to about 50% by weight of said composition of water, from about 5% to about 10% by weight of said composition of sodium cocoisethionate, and from about 5% to about 10% by weight of said composition of at least one emollient selected from the group consisting of polyethylene glycol, fatty acid esters of polyethylene glycol, dimethicone, and alkyl esters of fatty acids; and said suspending agent is bentonite.

8. The method of claim 7 wherein the topical composition is applied several times daily.

* * * * *